United States Patent
Uhrlandt et al.

(10) Patent No.: US 6,960,251 B2
(45) Date of Patent: *Nov. 1, 2005

(54) INHOMOGENEOUS SILICAS AS CARRIER MATERIAL

(75) Inventors: Stefan Uhrlandt, Niederkassel (DE); Ralf Schmoll, Bonn (DE); Claus-Peter Drexel, Neu-Isenburg (DE)

(73) Assignee: Degussa AG, Duesseldorf (DE)

( * ) Notice: Subject to any disclaimer, the term of this patent is extended or adjusted under 35 U.S.C. 154(b) by 313 days.

This patent is subject to a terminal disclaimer.

(21) Appl. No.: 10/098,594

(22) Filed: Mar. 18, 2002

(65) Prior Publication Data

US 2003/0059380 A1 Mar. 27, 2003

(30) Foreign Application Priority Data

Mar. 16, 2001 (DE) .......................................... 101 12 651

(51) Int. Cl.[7] .............................................. C04B 14/04
(52) U.S. Cl. ...................... 106/482; 106/481; 106/482; 423/335
(58) Field of Search ................................ 106/481, 482; 423/335

(56) References Cited

U.S. PATENT DOCUMENTS

| | | | | |
|---|---|---|---|---|
| 5,110,574 A | * | 5/1992 | Reinhardt et al. | ........... 423/335 |
| 6,613,309 B2 | * | 9/2003 | Uhrlandt et al. | ............... 424/49 |
| 6,702,887 B2 | * | 3/2004 | Uhrlandt et al. | ............. 106/482 |

FOREIGN PATENT DOCUMENTS

| | | |
|---|---|---|
| EP | 0 268 763 | 6/1988 |
| EP | 0 272 380 | 6/1988 |
| EP | 0 942 029 | 9/1999 |
| JP | 8-133720 | 5/1988 |
| WO | WO 99/49850 | 10/1999 |

OTHER PUBLICATIONS

Patent Abstracts of Japan, JP 8–133720, May 25, 1996.
Patent Abstracts of Japan, JP 6–001605, Jan. 11, 1994.
U.S. Appl. No. 10/522,672, filed Jan. 28, 2005, Uhrlandt et al.
U.S. Appl. No. 10/523,414, filed Feb. 3, 2005, Uhrlandt et al.
U.S. Appl. No. 10/523,029, filed Feb. 2, 2005, Uhrlandt et al.
U.S. Appl. No. 11/058,293, filed Feb. 16, 2005, Blume et al.
U.S. Appl. No. 10/098,594, filed Mar. 18, 2002, Uhrlandt et al.
U.S. Appl. No. 10/516,308, filed Dec. 10, 2004, Uhrlandt et al.

* cited by examiner

*Primary Examiner*—J. A. Lorengo
*Assistant Examiner*—S. S. Manlove
(74) *Attorney, Agent, or Firm*—Oblon, Spivak, McClelland, Maier & Neustadt, P.C.

(57) ABSTRACT

A silica comprising at least two silica fractions, wherein said at least two silica fractions differ by at least 10% in at least one value for BET surface area, CTAB surface area and DBP absorption, the ranges of these three physicochemical properties being as follows:

| | |
|---|---|
| BET surface area | 100–900 m²/g, |
| CTAB surface area | 100–500 m²/g, |
| DBP absorption | 150–350 g/100 g. |

23 Claims, No Drawings

INHOMOGENEOUS SILICAS AS CARRIER MATERIAL

BACKGROUND OF THE INVENTION

1. Field of the Invention

The present invention relates to silicas having an inhomogeneous structure or composition, to processes for preparing them, and to their use as carrier material.

2. Description of the Background

Readily dispersible silicas are prepared, for example, by the procedure described, for instance, in EP 0 901 986 or EP 0 647 591 by precipitating waterglass with sulfuric acid, followed by drying. The dried products are subsequently ground and/or granulated.

By means of mechanical granulation, any silica can be prepared in dust-free form;
however, this additional process step generally brings about a deterioration in the dispersibility of the silica.

In another process, silicas are prepared, likewise by acid precipitation, but are dried by spraying with hot air and at the same time are shaped into beads, which are easily destroyed. Thus EP 018 866 describes the preparation of spray-dried silica having an average particle diameter of more than 80 µm, the particles being solid and possessing a homogeneous structure.

Spray-dried silicas as described in EP 0 018 866 are particularly suitable as carrier materials, because they are dust-free and possess a high absorbency. The ability to operate without dust being generated is an important criterion for the processing of the silica, because simple processing of the silicas without the need for suction exhaust units is of great economic importance. Besides freedom from dust, the specific surface areas (BET, CTAB) and the oil absorption capacity (DBP) are important for carrier material utility.

In contrast to mechanical granulation, spray drying cannot be used to prepare all silicas in dust-free form.

One type of silica generally does not meet all of the required criteria. Mixtures of two or more types of silica can frequently be prepared, but such mixtures normally generate excessive amounts of dust. A need therefore continues to exist for a silica which at one and the same time covers broad ranges of physicochemical data such as BET or CTAB surface area, and which has good absorbency and generates only low quantities of dust. As already stated, this cannot be achieved for all silicas by means of spray drying or granulation.

SUMMARY OF THE INVENTION

Accordingly, one object of the present invention is to provide a silica that has an inhomogeneous composition and is readily adjustable to meet the requirements that are called for as a carrier and yet has good absorbency and a low fines content.

Briefly, this object and other objects of the present invention as hereinafter will become more readily apparent can be attained by a silica comprising at least two silica fractions, wherein said at least two silica fractions differ by at least 10% in at least one value for BET surface area, CTAB surface area and DBP absorption, the ranges of these three physicochemical properties being as follows:

| | |
|---|---|
| BET surface area | 100–900 m$^2$/g, |
| CTAB surface area | 100–500 m$^2$/g, |
| DBP absorption | 150–350 g/100 g. |

DETAILED DESCRIPTION OF THE PREFERRED EMBODIMENTS

The silicas of the invention are particularly suitable for use as carrier materials for active substances such as vitamins and choline chloride, for example.

The composition of the silicas, comprising at least two silica fractions, results in a structural inhomogeneity of the silica, which is reflected at the same time in good absorbency and a low fines content and provides the physicochemical data required of the present invention.

Silicas of the invention possess a fines content of not more than 10% with a particle diameter of less than or equal to 63 µm (Alpine sieve residue).

A similar concept is described in EP 0 942 029. There, compositions are described which comprise a precipitated silica in two different aggregate sizes. The different aggregate sizes are employed for the ready dispersibility of the silica in a rubber blend. The different silica fractions of the present invention are not described in these publications; moreover, in the present case a different aggregate size of the silica fractions is of secondary importance. What is of importance in the invention is the differences in the physicochemical data of the two silicas. The use of silicas as carrier materials is not described in EP 0 942 029.

For the purpose of the present invention, a silica fraction refers to different grades of silicas which, owing to different preparation processes or process variants, have a difference of 10% in at least one of the abovementioned physicochemical characteristics. Such a difference exists preferably for two, particularly preferable three, of these parameters.

The differences in the abovementioned parameters may be obtained by means of different processes of preparing the silica fractions. Accordingly, all, one or more of the silica fractions may be precipitated silicas and/or pyrogenic silicas. In the case of precipitated silicas in particular it is possible to obtain different silica fractions by means of different precipitation processes. Silicas of the invention may also be prepared from fractions of precipitated and pyrogenic silicas.

For precipitated silicas as carrier material, a variety of precipitation methods is known and are disclosed, for example, in EP 0 937 755 and EP 0 643 015. In the examples of the two documents, illustratively, two precipitated silicas from different preparation processes are processed to give inhomogeneous silicas. Such methods can be used in the present invention. It is also possible to combine hydrophobicized silica fractions with untreated silica fractions to give the silica of the invention.

The silica fractions may be precipitated silicas or pyrogenic silicas, and the fractions may be mixed at different steps in the process that are normally conducted in the preparation of silicas.

When using fractions of precipitated silicas, mixing may take place following the precipitation of silicate with an acid, which is normally waterglass, i.e., sodium silicate, with sulfuric acid, by mixing together the precipitation suspensions or the filtercakes obtained following filtration of the suspensions, and also liquefied (resuspended) filtercakes. It is also possible to add ready-prepared, dried or hydrophobicized silica fractions, as solids, to the suspensions or to the filtercakes.

The mixtures obtained in this manner may need to be filtered and dried by a usual technique. Examples of drying processes are spray drying, nozzle spray drier, rack drier, rotary tube drier, and spin flash drier processes.

Drying may be followed by a final grinding and/or granulation step.

It is also possible to mix the silica fractions in the dry state. This operation may be followed by resuspension, with the above drying steps, and/or by grinding/granulation.

Silicas of the invention may have the following physicochemical data:

| | |
|---|---|
| BET surface area | 100–900 m$^2$/g, preferably 150–600 m$^2$/g |
| CTAB surface area | 100–500 m$^2$/g, preferably 150–400 m$^2$/g |
| DBP absorption | 150–350 g/100 g |

These physicochemical data relate to the silica of the invention per se, and not to the silica fractions.

In the manner described, the physicochemical data of the silica fractions must differ by at least 10%, preferably by at least 15%, and particularly preferred by at least 20%.

The physicochemical data are determined by the following methods:

| | |
|---|---|
| BET surface area | Areameter, from Ströhlein, to ISO 5794/Annex D |
| CTAB surface area | at pH 9 by the method of Jay, Janzen and Kraus in Rubber Chemistry and Technology 44 (1971) 1287 |
| DBP number | ASTM D 2414-88 |

The invention in addition provides a process for preparing silicas comprising at least two silica fractions, in which at least two silica fractions differ by at least 10% in at one least one value for BET surface area, CTAB surface area and DBP absorption. The fractions are mixed with one another.

The proportion of the respective fractions in the suspension or of the silica should in each case range from 5 to 95% by weight, based on the dry silica.

The silica is preferably prepared, by spray drying, for example, in a particle form having an average diameter of more than 80 µm, in particular more than 100 µm, particularly preferably more than 200 µm. The suspension may be spray-dried as described, for example, in U.S. Pat. No. 4,097,771.

The silicas of the invention may therefore be used as carrier material, especially for adsorbing liquid active substances.

The silicas of the invention can be used in particular as carriers for vitamins (A, B, C, E), where appropriate in acetate form, proteins, enzymes, choline chloride and the like.

Furthermore, the silica may be used as a support for catalytically active substances.

Moreover, the silicas of the invention may be used in all areas of application in which silicas are customarily used, such as in battery separators, antiblocking agents, flatting agents and paints, paper coating slips or defoamers, for example.

The silica of the invention or the silica fractions may be modified in a known manner, i.e., hydrophobicized, with silanes, with silicone oil and/or with organosilanes.

Procedure for Determining the Alpine Sieve Residue

To determine the sieve residue, the silica or silicate sample is passed through a 500 µm sieve in order to destroy any devolatilization agglomerates that may be present. Then 10 g of the sieved sample are placed on the air jet sieve, with a 63 µm sieve mesh, and are sieved at 200 mm water column under pressure. Particles of silica or silicate which settle on the sieve cover of the apparatus are removed by careful tapping on the button of the sieve cover. The sieving operation generally lasts 5 minutes. It is at an end when the residue remains constant, generally evident from the free-flowing appearance. Sieving is then continued for one more minute in order to be on the safe side.

If any agglomerates form, the sieving operation is briefly interrupted and the agglomerates are broken down under gentle pressure using a brush. After sieving, the sieve residue is carefully removed from the air jet sieve and reweighed. The sieve residue is expressed in percent, always in conjunction with the mesh size of the sieve.

Calculation $$\% \text{ of sieve residue} = \frac{A \cdot 100}{E}$$

A=final weight in g
E=initial weight in g
Apparatus
Alpine air jet sieve, laboratory type S 200
Vacuum cleaner or fan
Air jet sieve with sieve mesh 63 µm to DIN 4188
Precision balance Having generally described this invention, a further understanding can be obtained by reference to certain specific examples which are provided herein for purposes of illustration only and are not intended to be limiting unless otherwise specified.

Two silica fractions were prepared, A in accordance with the procedure described in British Patent 1,043,282 or DE 24 47 013 and B in accordance to the procedure described in DE 31 44 299, and the suspensions obtained from the precipitations were reacted further in the manner described below.

EXAMPLES

Example 1

The precipitation suspensions of the silica fractions A and B were mixed in a 50:50 ratio. This was done by mixing 80 kg of the precipitated silica A (solids content approximately 46 g/l) with 80 kg of the precipitated silica B (solids content approximately 64 g/l) in a stirred vessel. The resulting mixture was filtered and the filtercake was liquefied with a small amount of acid and sprayed in a nozzle spray drier. The analytical data obtained are compiled in Table 1.

Example 2

The precipitation suspensions of the silica fractions A and B were mixed in a 70:30 ratio. This was done by mixing 112 kg of the precipitated silica A (solids content approximately 46 g/l) with 48 kg of the precipitated silica B (solids content approximately 64 µl) in a stirred vessel. The resulting mixture was filtered and the filtercake was liquefied with a small amount of acid and sprayed in a nozzle spray drier. The analytical data obtained are compiled in Table 1.

Example 3

The precipitation suspensions of the silica fractions A and B were mixed in a 30:70 ratio. This was done by mixing 43.8 kg of the precipitated silica A (solids content approximately 46 g/l) with 102.2 kg of the precipitated silica B (solids content approximately 64 g/l) in a stirred vessel. The resulting mixture was filtered and the filtercake was liquefied with a small amount of acid and sprayed in a nozzle spray drier. The analytical data obtained are compiled in Table 1.

Example 4

A mixture of the dried silica fractions (50:50) was prepared.

Flowability of a Choline Chloride Adsorbate

In addition to a high absorption capacity for liquids, it is necessary that the resulting adsorbates be readily flowable. As an example, a 50% adsorbate of choline chloride on the corresponding silica was prepared from 66.6 g of a 75% strength aqueous choline chloride solution and 33.3 g of the respective silica, and the flowability was assessed by means

TABLE 1

Comparison of the analytical data from Examples 1–4 and of silica fractions A and B:

|  |  | Silica fraction A | Silica fraction B | Differences of fractions A:B in % | Example 1 | Example 2 | Example 3 | Example 4 |
|---|---|---|---|---|---|---|---|---|
| Loss on ignition, DIN | % | 5.0 | 5.0 |  | 3.7 | 2.7 | 3.4 | 10.1 |
| Water content | % | 5.0 | 4.5 | 10 | 5.3 | 5.3 | 5.5 | 5.6 |
| pH reading |  | 6.5 | 6.0 | 7.6 | 6.2 | 6.4 | 6.4 | 6.6 |
| Conductivity | $\mu S$ | 800 | 700 | 12.5 | 600 | 740 | 610 | 750 |
| BET surface area | $m^2/g$ | 195 | 195 | 00 | 354 | 403 | 284 | 302 |
| CTAB surface area | $m^2/g$ | 175 | 350 | 50 | 271 | 302 | 232 | 256 |
| DBP absorption | g/100 g | 263 | 335 | 21.5 | 281 | 287 | 265 | 296 |
| Tapped density | g/l | 280 | 180 | 36.7 | 200 | 185 | 217 | 222 |
| Alpine sieve residue 63 $\mu m$ | % | 80 | >=20 |  | 99 | 91 | 99 | 52 |
| Alpine sieve residue 180 $\mu m$ | % | >=4 | 1 |  | 82 | 18 | 87 | 4.5 |
| Alpine sieve residue 250 $\mu m$ | % | n.d. | n.d. |  | 75 | 1.1 | 48 |  |

Performance Properties of the Silica of the Invention
Flow Properties of the Silica The products prepared in accordance with the invention, of Examples 1–3, have very good intrinsic flowability.

of glass efflux vessels and the conical bed height. The inhomogeneous silica s DTT 3120 and DTT 3140 give advantages over standard silicas here (Hubersil 5170).

|  | Method | Unit | Description of method | Silica of Ex. 1 | Silica of Ex. 2 | Silica of Ex. 3 |
|---|---|---|---|---|---|---|
| Flow property | Glass efflux vessel | (score) |  | 1 | 1 | 1 |
|  | Conical bed height | [mm] |  | 9 | 13 | 8 |

Maximum Choline Chloride Absorption

The maximum choline chloride absorption provides important information on the absorption capacity of a silica. Since more highly concentrated adsorbates are of advantage, the desire is for as high an absorption capacity as possible. The maximum choline chloride absorption of the inhomogeneous silicas is much higher than in the case of prior art silica products.

|  | Method | Unit | Silica of Ex. 1 | Silica of Ex. 2 | Silica of Ex. 3 | Comp. Ex. Hubersil 5170 |
|---|---|---|---|---|---|---|
| Flow property 50% choline chloride adsorbate | Glass efflux vessel | (score) | 2 | 5 | 1 | 6 |
|  | Conical bed height | [mm] | 18 | 32 | 24 | >50 |

Agglomerate Content

The agglomerate content gives important information on whether a silica is suitable for use as a carrier substance. A high agglomerate content is undesirable, since it leads to an adsorbate which is difficult to process. The agglomerate content of a 50% choline chloride concentrate prepared from 100 g of the corresponding silica and 200 g of a 75% strength aqueous choline chloride solution, is very low, at

| Method | Unit | Silica of Ex. 1 | Silica of Ex. 2 | Silica of Ex. 3 | Silica of Ex. 4 | Comp. Ex. Sipernat 2200 | Comp. Ex. Sipernat 22 | Comp. Ex. Hubersil 5170 |
|---|---|---|---|---|---|---|---|---|
| Maximum choline chloride absorption | [g/100 g] | 300 | 295 | 268 | 280 | 245 | 240 | 165 |

0.3–2.1%, for the inhomogeneous silicas investigated. The comparative silicas have much higher agglomerate contents.

| | Method | Unit | Silica of Ex. 1 | Silica of Ex. 2 | Silica of Ex. 3 | Comp. ex. Sipernat 2200 | Comp. ex. Sipernat 22 | Comp. ex. HiSil SC72 |
|---|---|---|---|---|---|---|---|---|
| 50% adsorbate of choline chloride on Silica | Agglomerate content | [%] | 1.3 | 2.1 | 0.3 | 3.7 | 2.8 | 2.7 |

Sorption Rate

Another important parameter for the application is the sorption rate, since in the industrial production of adsorbates the objective is for high throughputs and thus short residence times in the mixer. In the case of the inhomogeneous silicas investigated, the sorption rate for vitamin E acetate is better than that of the comparative products Sipernat 2200 and Hubersil 5170.

| | Method | Unit | Silica of Ex. 1 | Silica of Ex. 2 | Silica of Ex. 3 | Silica of Ex. 4 | Comp. Ex. Sipernat 2200 | Comp. Ex. Hubersil 5170 |
|---|---|---|---|---|---|---|---|---|
| Sorption rate vitamin E acetate | | (score) | 2.5 | 2.5 | 3.0 | 2.0 | 4.5 | 5 |

The methods of measuring the flow properties, choline chloride absorption, agglomerate content, and sorption rate are in accordance with the procedures described in "Synthetische Pigmente als Fließhilfsmittel und als Trägersubstanz" [Synthetic pigments as flow aids and carriers], Pigments Brochure Series Nos. 31, Degussa AG, 1992, and also Nos. 1 and 30.

The results of the investigation demonstrate that the inhomogeneous carrier silicas of the invention are suitable for preparing highly concentrated adsorbates, are readily flowable, and produce little dust. This is demonstrated from the example of the absorption of vitamin E acetate and 75% strength aqueous choline chloride solution. Both products are used in the adsorbate form in the feed industry. Also conceivable in practice is the preparation of other highly concentrated adsorbates, such as melamine resins (additive in the rubber industry), acids, e.g., formic or phosphoric acid (feed industry), and pigments, e.g., tagetes extracts (feed industry).

The disclosure of German priority application 10112651.4 filed Mar. 16, 2001 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A silica comprising at least two silica fractions, wherein said at least two silica fractions differ by at least 10% in at least one value for BET surface area, CTAB surface area and DBP absorption, the ranges of these three physicochemical properties being as follows:

| | |
|---|---|
| BET surface area | 100–900 m$^2$/g, |
| CTAB surface area | 100–500 m$^2$/g, |
| DBP absorption | 150–350 g/100 g. |

2. The silica as claimed in claim 1, which is in the form of particles having an average diameter of more than 80 μm.

3. The silica as claimed in claim 1, wherein the respective proportion of one silica fraction in the silica ranges from 5 to 95% by weight.

4. The silica as claimed in claim 1, which is hydrophobicized.

5. The silica as claimed in claim 1, wherein at least one silica fraction is hydrophobicized.

6. The silica as claimed in claim 1, wherein one or more silica fractions comprise a precipitated silica.

7. The silica as claimed in claim 1, wherein the silica fractions are prepared by precipitating a silicate with an acid and the resulting precipitation suspensions are mixed.

8. The silica as claimed in claim 1, wherein the silica fractions are prepared by precipitating silicate with an acid, the precipitation suspension is filtered, and the resulting filtercakes are mixed.

9. The silica as claimed in claim 1, wherein the silica fractions are prepared by precipitating silicate with an acid, the filtercakes or ready-dried silica are liquefied, and the resulting suspensions are mixed.

10. The silica as claimed in claim 1, wherein one or more silica fractions comprise a pyrogenic silica.

11. The silica as claimed in claim 1, wherein the silica fractions are mixed in the dried state.

12. A process for preparing silicas comprising at least two silica fractions, which comprises:
 mixing at least two silica fractions with one another which differ by at least 10% in at least one value for the BET surface area, the CTAB surface area and the DBP absorption.

13. The process as claimed in claim 12, wherein the silica is in the form of particles having an average diameter of more than 80 μm.

14. The process as claimed in claim 12, wherein the values of the physicochemical properties of the silica are as follows:

| | |
|---|---|
| BET surface area | 100–900 m$^2$/g, |
| CTAB surface area | 100–500 m$^2$/g, |
| DBP absorption | 150–350 g/100 g. |

15. The process as claimed in claim 13, wherein the respective proportion of one silica fraction in the silica ranges from 5 to 95% by weight.

16. The process as claimed in claim 13, wherein the silica is hydrophobicized.

17. The process as claimed in claim 13, wherein at least one silica fraction is hydrophobicized.

18. The process as claimed in claim 13, wherein one or more silica fractions comprise a precipitated silica.

19. The process as claimed in claim 13, wherein the silica fractions are prepared by precipitating silicate with an acid and the resulting precipitation suspensions are mixed.

20. The process as claimed in claim 13, wherein the silica fractions are prepared by precipitating silicate with an acid, the precipitation suspension is filtered, and the resulting filtercakes are mixed.

21. The process as claimed in claim 13, wherein the silica fractions are prepared by precipitating silicate with an acid, the filtercakes or ready-dried silica are liquefied, and the resulting suspensions are mixed.

22. The process as claimed in claim 13, wherein one or more silica fractions comprise a pyrogenic silica.

23. The process as claimed in claim 13, wherein the silica fractions are mixed in the dried state.

* * * * *